United States Patent [19]

Jung et al.

[11] Patent Number: 5,138,080
[45] Date of Patent: Aug. 11, 1992

[54] POLYSILAMETHYLENOSILANES AND PROCESS FOR THEIR PREPARATION

[75] Inventors: Il-Nam Jung; Gyu-Hwan Lee; Seung-Ho Yeon; Mi-Yeon Suk, all of Seoul, Rep. of Korea

[73] Assignee: Korea Institute of Science and Technology, Seoul, Rep. of Korea

[21] Appl. No.: 813,231

[22] Filed: Dec. 23, 1991

[30] Foreign Application Priority Data

Feb. 25, 1991 [KR] Rep. of Korea ................ 3019/1991

[51] Int. Cl.$^5$ .............................................. C07F 7/08
[52] U.S. Cl. .................................... 556/430; 528/12; 528/34
[58] Field of Search ..................... 556/430; 528/12, 34

[56] References Cited

U.S. PATENT DOCUMENTS

| | | | |
|---|---|---|---|
| 4,414,403 | 11/1983 | Schilling et al. | 556/430 |
| 4,590,253 | 5/1986 | Hasegawa et al. | 556/430 X |
| 4,962,175 | 10/1990 | Bujalski et al. | 556/430 X |
| 4,962,176 | 10/1990 | Bujalski et al. | 556/430 X |
| 5,087,685 | 2/1992 | Sartori et al. | 556/430 X |

*Primary Examiner*—Paul F. Shaver
*Attorney, Agent, or Firm*—Townsend and Townsend

[57] ABSTRACT

The invention is concerned with novel polysilamethylenosilane polymers having polysilane-polycarbosilane skeleton which can be prepared in one-step reaction from mixtures of chlorosilaalkanes and organochlorosilanes with alkali metals in one of appropriate solvents or in combination of solvents thereof. Such polysilamethylenosilane polymers are soluble and thermoplastic, and can be pyrolyzed to obtain improved yields of silicon carbide at atmospheric pressure.

6 Claims, No Drawings

POLYSILAMETHYLENOSILANES AND PROCESS FOR THEIR PREPARATION

BACKGROUND OF THE INVENTION

The present invention relates to novel polysilamethylenosilane polymers having polysilane-polycarbosilane skeleton, as represented by formula (III), to their production from selected chlorosilaalkanes as represented by formula (I) or a mixture of the chlorosilaalkanes and organochlorosilanes such as dimethyldichlorosilane and organotrichlorosilanes as represented by formula (II), and to their use in the production of silicon carbide:

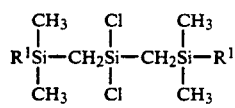

wherein, $R^1$ represents methyl or chlorine atom,

wherein, $R^2$ represents alkyl group containing from 1 to 18 carbon atoms, allyl, vinyl, phenyl, trimethylsilylmethyl groups,

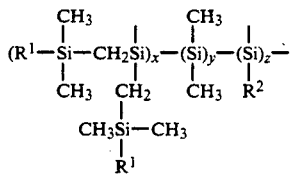

wherein, $R^1$ represents $CH_3$ when $R^1$ in formula (I) is methyl, while $R^1$ represents Si-Si bond when $R^1$ in formula (I) is Cl; $R^2$ is alkyl group containing from 1 to 18 carbon atoms, aryl group, vinyl, phenyl, trimethylsilylmethyl groups and x, y, z are arbitrary constants.

The polysilamethylenosilane polymers can be prepared in one-step reaction from mixtures of chlorosilaalkanes and organochlorosilanes with alkali metal in one of appropriate solvents or in combination of solvents thereof. The solvents for dechlorination reaction can be toluene, xylene, benzene, tetrahydrofuran or mixture of solvents thereof. Toluene is the most preferable solvent and 80 to 20 mixture of toluene and tetrahydrofuran is most preferable as mixed solvent. Lithium, sodium, potassium or alloy of sodium and potassium can be used as the alkali metal for dechlorination. Such polysilamethylenosilane polymers are soluble and thermoplastic, and can be pyrolyzed to obtain improved yields of silicon carbide at atmospheric pressure.

DESCRIPTION OF THE PRIOR ART

The first dimethylpolysilane was prepared from dimethyldichlorosilane and active metals by Burkhard in 1949 (C. A. Burkhard, *J. Am. Chem. Soc.*, 71, 964 (1949)). It is an insoluble, infusible, intractable white solid and decomposes before melting. Because of the difficulty with characterization, it had not been of technically importance until around 1975.

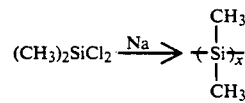

In 1975, Yajima et at., reported that dimethylpolysilane could be thermolyzed at 470° C. to produce a carbosilane polymer (S. Yajima, K. Okamura, J. Hayashi, and M. Omor, *J. Am. Ceram. Soc.*, 59, 324 (1976))

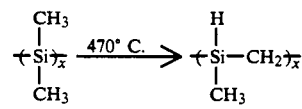

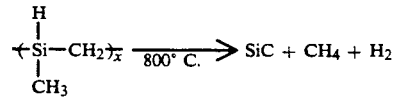

The carbosilanes are, generally, soluble in organic solvents such as ether, THF, toluene, or benzene and can be melted, molded, cast into films or drawn into fibers. The crude polycarbosilanes produced from the thermolysis of dimethylpolysilanes are then fractionated from solvents, spun into fibers, oxidized on the surface with air to give infusibility and flexibility, and finally pyrolyzed at 800°–1350° C. to produce silicon carbide.

Sodium is widely used for dechlorination of organochlorosilanes for reasons of low cost, commercial availability, low hazard level compared to potassium. Other active metals, such as potassium, lithium, and magnesium are more costly. Although the potassium-sodium alloy containing about 78% potassium is liquid and easy to handle, it is also cost more than sodium by itself. The sodium is normally introduced to the reaction as a dispersion in an inert solvent such as toluene or xylene and used in about 20% excess relative to Si-Cl mole numbers.

The solvent medium for dechlorination is the predried solvent or mixture thereof unreactive with chlorosilanes or sodium, which has a boiling point above the melting point of sodium metal, i.e., 98° C. The reaction temperature should also be maintained above the melting point of sodium metal. It is preferred to be vigorously stirred to prevent from caking of by-product salts. After cooling reactions may be terminated by addition of dilute aqueous THF or other protic materials such as low molecular weight alcohols or carboxylic acids. Hydrogen gas evolves during the quenching process, which explodes in contact with air or oxygen. The yield of dimethylpolysilane by dechlorination of dimethyldichlorosilane is in the range of from 60 to 70% at maximum. The hazardness of alkali metal use and the hydrogen evolution make the mass production difficult. The low yield of dimethylpolysilane also makes the process economically less feasible.

In U.S. Pat. No. 4,260,780 and 4,324,901, West discloses the preparation of methylphenylpolysilane polymers by addition of a small amount of methylphenyldichlorosilane to dimethyldichlorosilane and followed by reduction of the resulting mixture with active metals such as sodium or sodium-potassium alloy. The resulting polymer is soluble in organic solvents and it is a gum or meltable resinous material. When the polysilane is soluble in the cooled reaction medium, the reaction mixture can be filtered without quenching to remove any excess of sodium prior to precipitation. The formation of soluble and meltable polysilanes offers the improved yields and the possibility of preparing silicon carbide directly from the polysilane, rather than going through another synthesis step of polycarbosilane.

The above methylphenylpolysilane copolymers, which are prepared in one step, are rich in phenyl groups, and do yield silicon carbide compositions on unconfined pyrolysis. However, the SiC yield is substantially low compared with that obtained from the pyrolysis of polycarbosilanes. These phenyl rich copolymers are also reported to be photoactive, i.e., to be crosslinked on exposure to light, which may lead to significant processing and shelf life limitation.

$$x(CH_3)_2SiCl_2 + yPh(CH_3)SiCl_2 \xrightarrow{Na}$$

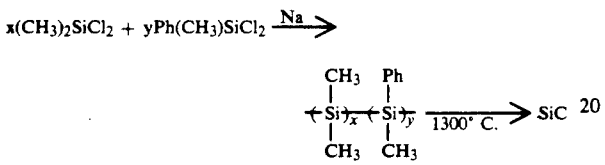

In U.S. Pat. No. 4,414,403, Schilling discloses that branched polycarbosilanes can be prepared in one step from silane monomers alone or mixtures thereof containing vinyl and halo or halomethyl moieties. The branched polycarbosilanes are pyrolyzed and directly converted to silicon carbide at atmospheric pressure. In U.S. Pat. No. 4,472,591, he also discloses that the hydrosilyl organosilicon polymers having vinyl groups provide in situ branching during the pyrolysis to silicon carbide and give significantly improved SiC yield. This method has advantages of simpler process and higher ceramic yields over Yajima method. However, the silicon carbide produced by this process contains the excess of free carbon which comes from the two methylene groups between two backbone silicon atoms.

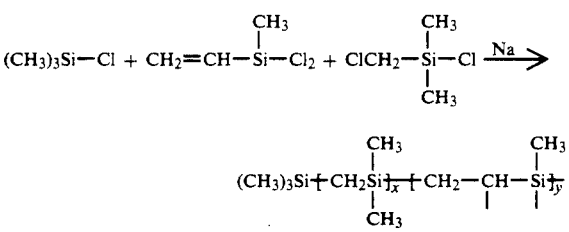

DETAILED DESCRIPTION OF THE INVENTION

In the present invention, polysilamethylenosilane polymers having polysilane-polycarbosilane skeleton are prepared by dechlorination of chlorosilaalkanes, or mixtures of chlorosilaalkanes with other chlorosilanes, using sodium metal in one of appropriate solvents or in combination with solvents thereof. Chlorosilaalkanes may be represented by the formula (I):

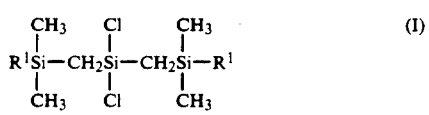

wherein, $R^1$ represents methyl or chlorine atom.

The chlorosilanes which are incorporated with chlorosilaalkanes in the dechlorination reactions may be dimethyldichlorosilane or organotrichlorosilane as represented by the formula (II):

wherein, $R^2$ is alkyl group containing from 1 to 18 carbon atoms, phenyl, allyl, vinyl, trimethylsilylmethyl groups.

Preferred chlorosilaalkanes include, but are not limited to, 2,4,4,6-tetrachloro-2,6-dimethyl-2,4,6-trisilaheptane and 2,2,4,4,6,6-hexachloro-2,4,6trisilaheptane. The other chlorosilanes include, but are not limited to, methyltrichlorosilane, phenyltrichlorosilane, vinyltrichlorosilane, allyltrichlorosilane, (trimethylsily)methyl trichlorosilane, octadecyltrichlorosilane, dimethyldichlorosilane, methyldichlorosilane, chloromethylmethyldichlorosilane and trimethylchlorosilane.

Mironov et al. reported that 2,4,6-trisilaheptanes could be prepared by reacting chloromethylsilanes as represented by formula (IV) with silicon in the presence of copper catalyst (V. F. Mironov, T. E. Gar and A. A. Buyakov, Zh. Obsch. Khim., 42, 1362 (1972)). However, they did not obtain trisilaheptanes as the major products. Disilaalkanes were the major products due to the decomposition of the starting material. Jung et al. reported that the trisilaheptanes could be obtained as the major products from the direct reaction of chloromethylsilanes with silicon in the presence of copper catalyst, using the stirred reactor equipped with a spiral band agitator or a fluidized reactor at the carefully controlled reaction temperature of below 350° C. (Korean Patent Application Number 1055 (1991. 1. 22)).

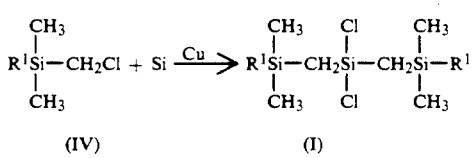

wherein, in formulas (I) and (IV), $R^1$ represents methyl or chlorine atom.

The polysilamethylenosilane producing reactions of the present invention can be run in standard laboratory glasswares or commercial equipments, under inert atmosphere at atmospheric pressure, with units for external heating and cooling, stirring, and for incremental addition of mixtures of the start chlorosilaalkanes and organosilanes. Thus, the polymerization process of the present invention is not critical with regard to equipments and pressure.

In a typical preparation, a certain amount of sodium metal is placed in the predried solvent under inert atmosphere. The solution is heated to reflux, and melt the sodium and the solution is stirred to make the sodium dispersed. The mixture of chlorosilanes is added to the solution. In certain cases, each different chlorosilane may be added sequentially, rather than as mixture. The reactions may be sufficiently exothermic at controlled addition rates to maintain to reflux without continuous carring out external heating. After completion of addition, heating may be carried out for a certain period of time to complete the dechlorination. The reaction temperature should be maintained above the melting point of sodium and be vigorously stirred to prevent from caking of by-product salts. The solids are removed by filtration after cooling the solution.

The form of products may vary from low viscosity fluids to insoluble solids depending on the starting silicon compounds chosen and their mixing ratios. The preferred products are soluble and thermoplastic polymers and can be transformed and dissolved in various solvents for melt spinning, solution spinning, or casting of films.

The products are convertable to silicon carbide simply by heating composition alone or in combination with other components at an appropriate rate to 1200° C. or above.

In the preparation of the polysilamethylenosilane according to the present invention, chlorosilaalkanes represented by formula (I) can be polymerized by themselves or be copolymerized with the other chlorosilanes, such as dimethyldichlorosilane, in the amounts of up to 75 mole percent. Further, organotrichlorosilanes represented by formula (II) may be incorporated in the mixture of the above-mentioned chlorosilanes in order to control the molecular weights and solubilities of the thus obtained products. The copolymerization reaction may be represented as the following reaction scheme.

-continued
Reaction Scheme

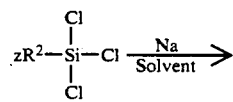

(II)

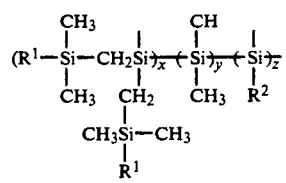

(III)

In formula (III), $R^1$ represents $CH_3$ when $R^1$ in formula (I) is methyl, while $R^1$ represents Si—Si bond when $R^1$ in formula (I) is Cl; $R^2$ is alkyl group containing from 1 to 18 carbon atoms, aryl, vinyl, phenyl, or trimethylsilylmethyl groups and x, y, z are arbitrary constants.

The properties of the products according to the chlorosilane compositions are shown in Table 1.

TABLE 1

The properties of Polymers vs. Chlorosilane Compositions

| Organochlorosilane (mole %) | | | | Yields (%) | | Mol. weight |
|---|---|---|---|---|---|---|
| Formula (I) | | | Formula (II) | Soluble | Insoluble | |
| $R_1$ = Cl | $R_1$ = $CH_3$ | $Me_2SiCl_2$ | ($R_2$) | product | product | |
| 0 | 0 | 100 | | | 68 | — |
| 8 | 0 | 92 | | 24.1 | 26.3 | 7,000 |
| 25 | 0 | 75 | | 88.1 | | 2,000 |
| 44 | 0 | 56 | | 87.4 | | 4,400 |
| 80 | 0 | 20 | | 98.0 | | 11,000 |
| 100 | 0 | 0 | | 93.7 | | 27,000 |
| 25 | 0 | 70 | 5(Me) | 90.0 | | 4,900 |
| 25 | 0 | 65 | 10(Me) | 74.3 | | 3,300 |
| 20 | 0 | 75 | 5(Me) | 84.4 | | 2,300 |
| 25 | 0 | 70 | 5($Me_3Si\ CH_2$) | 92.9 | | 5,600 |
| 20 | 0 | 70 | 10(Me) | 87.3 | | 3,500 |
| 25 | 0 | 70 | 5(phenyl) | 91.3 | | 2,800 |
| 25 | 0 | 70 | 5(hexyl) | 89.0 | | 2,700 |
| 25 | 0 | 70 | 5(vinyl) | 93.0 | | 5,800 |
| 25 | 0 | 70 | 5(allyl) | 93.0 | | 3,700 |
| 45 | 0 | 60 | 15(Me) | 83.0 | | 4,000 |
| 0 | 25 | 75 | | 68.3 | 18.5 | 1,400 |
| 0 | 50 | 50 | | 97.5 | | 1,600 |
| 0 | 80 | 20 | | 97.0 | | 1,400 |
| 0 | 100 | 0 | | 97.3 | | 780 |
| 0 | 50 | 45 | 5(Me) | 81.1 | | 2,100 |
| 0 | 50 | 40 | 10(Me) | 93.3 | | 2,400 |
| 0 | 50 | 45 | 5(Ph) | 83.0 | | 1,800 |
| 0 | 50 | 45 | 5(hexyl) | 87.0 | | 1,800 |
| 0 | 50 | 45 | 5(vinyl) | 93.0 | | 2,200 |
| 0 | 50 | 45 | 5(allyl) | 92.0 | | 1,900 |
| 0 | 50 | 45 | 5($Me_3Si\ CH_2$) | 93.7 | | 2,300 |
| 50 | 50 | | | 92.7 | | 2,000 |
| 20 | 10 | 70 | | 92.0 | | 2,700 |
| 20 | 10 | 65 | 5(Me) | 87.6 | | 3,100 |
| 20 | 10 | 65 | 5(Ph) | 83.0 | | 3,200 |
| 20 | 10 | 65 | 5(vinyl) | 85.0 | | 4,100 |
| 20 | 10 | 65 | 5(octadecyl) | 89.0 | | 2,800 |
| 20 | 10 | 65 | 5(allyl) | 90.0 | | 3,900 |

Reaction Scheme

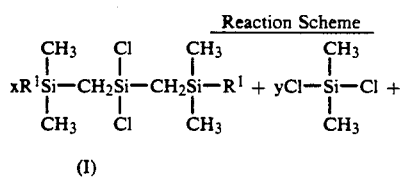

(I)

The invention is illustrated in the greater detail in the following examples which are not intended as limitations thereof.

EXAMPLE 1

500 ml three-neck flask was equipped with dropping funnel, condenser and mechanical stirrer. All the equipments were maintained under nitrogen atmosphere, so that the dried nitrogen passed through the end of the condenser. 120 ml of dried toluene was placed in the flask. 10 g (435 mmol) of metallic sodium was precisely cut and placed therein after washing with the dried toluene. In order to disperse metallic sodium as small size particles, toluene was in reflux using the electric mantle, while vigorously stirring the contents using the mechanical stirrer and then maintained for 30 minutes in such state. The mixture of 12.6 g (40 mmol) 2,4,4,6-tetrachloro-2,6-dimethyl-2,4,6-trisilaheptane and 15.5 g (120 mmol) dimethyldichlorosilane was placed therein through the dropping funnel over about 1 hr. After the solution was reacted under reflux for 8 hrs with stirring, the reaction products was not washed with alcohol and water and filtered through glass filter to separate the organic solution layer from the unreacted metallic sodium and sodium chloride. The filtered solid was washed with the dry-distilled toluene, and the solution was collected with the organic solution layer. This solution was distilled under reduced pressure to remove toluene as organic solvent. This product was very viscouse liquid. The amount of the obtained product was 12.18 g and the yield 88.1%. The product was very viscose liquid with milk colour, but slightly became clear as slowly heated. The GPC analysis result of this product represented by mean molecular weight of 11,000, and as the results analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$. As the analysis results by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 2

The same procedure as Example 1 was repeated except that 2,4,4,6-tetrachloro-2,6-dimethyl-2,4,6-trisilaheptane alone was reacted instead of the mixture of 2,4,4,6-tetrachloro-2,6-dimethyl-2,4,6-trisilaheptane and dimethyldichlorosilane. The yield of polysilamethylenosilane soluble in organic solvents was 93.7%, with mean molecular weight of 27,000. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$ and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 3

The materials used in Example 1 were reacted by the same conditions and procedure as Example 1 except that the mixing mole ratio of 2,4,4,6-tetrachloro-2,6-dimethyl-2,4,6-trisilaheptane and dimethyldichlorosilane was 44:56 instead of 25:75. The yield of polysilamethylenosilane soluble in organic solvents was 87.4%, with mean molecular weight of 4,400.

EXAMPLE 4

The materials used in Example 1 were reacted by the same conditions and procedure as Example 1 except that the mixing mole ratio of 2,4,4,6-tetrachloro-2,6-dimethyl-2,4,6-trisilaheptane and dimethyldichlorosilane was 8:92 instead of 25:75. The yield of polysilamethylenosilane soluble in organic solvents was 24.1%, with mean molecular weight of 7,000.

EXAMPLE 5

The materials used in Example 1 were reacted by the same conditions and procedure as Example 1 except that the mixing mole ratio of 2,4,4,6-tetrachloro-2,6-dimethyl-2,4,6-trisilaheptane and dimethyldichlorosilane was 80:20 instead of 25:75. The yield of polysilamethylenosilane soluble in organic solvents was 98%, with mean molecular weight of 11,000.

EXAMPLE 6

The materials used in Example 1 were reacted by the same conditions and procedure as Example 1 except that the mixing mole ratio of 2,4,4,6-tetrachloro-2,6-dimethyl-2,4,6-trisilaheptane and dimethyldichlorosilane was 25:70 instead of 25:75, and then was mixed with 5% of methyltrichlorosilane. The yield of polysilamethylenosilane soluble in organic solvents was 90%, with mean molecular weight of 4,900. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 7

The materials used in Example 6 were reacted by the same conditions and procedure as Example 6 except that the mixing ratio of 2,4,4,6-tetrachloro-2,6-dimethyl-2,4,6-trisilaheptane, dimethyldichlorosilane and methyltrichlorosilane in molar ratio was 25:65:10 instead of 25:70:5. The yield of polysilamethylenosilane soluble in organic solvents was 74.3%, with mean molecular weight of 3,300.

EXAMPLE 8

The materials used in Example 6 were reacted by the same conditions and procedure as Example 6 except that the mixing ratio was 20:75:5 instead of 25:70:5. The yield of polysilamethylenosilane soluble in organic solvents was 84.4%, with mean molecular weight of 2,300.

EXAMPLE 9

The materials used in Example 6 were reacted by the same conditions and procedure as Example 6 except that the mixing ratio was 20:70:10 instead of 25:70:5. The yield of polysilamethylenosilane soluble in organic solvents was 87.3%, with mean molecular weight of 3,500.

EXAMPLE 10

The materials used in Example 1 were reacted by the same conditions and procedure as Example 1 except that the mixing mole ratio of 2,4,4,6-tetrachloro-2,6-dimethyl-2,4,6-trisilaheptane and dimethyldichlorosilane was 25:70 instead of 25:75, and then was mixed with 5% of phenyltrichlorosilane. The yield of polysilamethylenosilane soluble in organic solvents was 91.3%, with mean molecular weight of 2,800. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, Si—H at 4.0 ppm and Si—Ph at 7.3 ppm.

EXAMPLE 11

The materials used in Example 10 were reacted by the same conditions and procedure as Example 10 except that 5% hexyltrichlorosilane was mixed instead of 5% phenyltrichlorosilane. The yield of polysilamethylenosilane soluble in organic solvents was 89.0%, with molecular weight of 2,700. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm and Si—C$_6$H$_{13}$ at 1.3 ppm.

EXAMPLE 12

The materials used in Example 10 were reacted by the same conditions and procedure as Example 10 except that 5% vinyltrichlorosilane was mixed instead of 5% phenyltrichlorosilane. The yield of polysilamethylenosilane soluble in organic solvents was 93.0%, with molecular weight of 5,800. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm and Si—CH=CH$_2$ at 6.0 ppm.

EXAMPLE 13

The materials used in Example 10 were reacted by the same conditions and procedure as Example 10 except that 5% allyltrichlorosilane was mixed instead of 5% phenytrichlorosilane. The yield of polysilamethylenosilane soluble in organic solvents was 93.0%, with molecular weight of 3,700. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm and Si—CH$_2$—CH=CH$_2$ at 5.0 and 5.8 ppm.

EXAMPLE 14

The materials used in Example 10 were reacted by the same conditions and procedure as Example 10 except that 5% trimethylsilylmethyltrichlorosilane was mixed instead of 5% phenyltrichlorosilane. The yield of polysilamethylenosilane soluble in organic solvents was 92.9%, with molecular weight of 5,600. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm.

EXAMPLE 15

The materials used in Example 6 were reacted by the same conditions and procedure as Example 6 except that the mixing mole ratio of 2,4,4,6-tetrachloro-2,6-dimethyl-2,4,6-trisilaheptane, dimethyldichlorosilane and methyltrichlorosilane was 25:60:15 instead of 25:70:5. The yield of polysilamethylenosilane soluble in organic solvents was 83.0%, with mean molecular weight of 4,000.

EXAMPLE 16

4,4-dichloro-2,2,6,6-tetramethyl-2,4,6-trisilaheptane instead of 2,4,4,6-tetrachloro-2,6-dimethyl-2,4,6-trisilaheptane, and dimethyldichlorosilane were conducted to react by the same conditions and procedure as Example 1. The yield of polysilamethylenosilane soluble in organic solvents was 68.3%, with mean molecular weight of 1,400. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 17

The materials used in Example 16 were reacted by the same conditions and procedure as Example 16 except that the mixing mole ratio of 4,4-dichloro-2,2,6,6-tetramethyl-2,4,6-trisilaheptane and dimethyldichlorosilane was 50:50 instead of 25:75. The yield of polysilamethylenosilane soluble in organic solvents was 97.5%, with mean molecular weight of 1,600. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 18

The materials used in Example 17 were reacted by the same conditions and procedure as Example 17 except that the mixing mole ratio of 4,4-dichloro-2,2,6,6-tetramethyl-2,4,6-trisilaheptane and dimethyldichlorosilane was 80:20 instead of 25:75. The yield of polysilamethylenosilane soluble in organic solvents was 97.0%, with mean molecular weight of 1,400.

EXAMPLE 19

The materials used in Example 16 were reacted by the same conditions and procedure as Example 16 except that the mixing mole ratio of 4,4-dichloro-2,2,6,6-tetramethyl-2,4,6-trisilaheptane and dimethyldichlorosilane was 50:45 instead of 25:75 and then was mixed with 5% of methlytriclorosilane. The yield of polysilamethylenosilane soluble in organic solvents was 81.1%, with mean molecular weight of 2,100. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 20

4,4-dichloro-2,2,6,6-tetramethyl-2,4,6-trisilaheptane instead of 2,4,4,6-tetrachloro-2,6-dimethyl-2,4,6-trisilaheptane was reacted by the same conditions and procedure as Example 2. The yield of polysilamethylenosilane soluble in organic solvents was 97.3%, with mean molecular weight of 780. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 21

The materials used in Example 19 were reacted by the same conditions and procedure as Example 19 except that the mixing mole ratio of 4,4-dichloro-2,2,6,6-tetramethyl-2,4,6-trisilaheptane, dimethyldichlorosilane and methyltrichlorosilane was 50:40:10 instead of 50:45:5. The yield of polysilamethylenosilane soluble in organic solvents was 93.3%, with mean molecular weight of 2,400. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 22

The materials used in Example 19 were reacted by the same conditions and procedure as Example 19 except that 5% phenyltrichlorosilane was mixed instead of 5% methyltrichlorosilane. The yield of polysilamethylenosilane soluble in organic solvents was 83.0%, with mean molecular weight of 1,800. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm, and Si—Ph at 7.3 ppm.

EXAMPLE 23

The materials used in Example 22 were reacted by the same conditions and procedure as Example 22 except that 5% hexyltrichlorosilane was mixed instead of 5% phenyltrichlorosilane. The yield of polysilamethylenosilane soluble in organic solvents was 87.0%, with molecular weight of 1,800. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm and Si—C$_6$H$_{13}$ at 1.3 ppm.

EXAMPLE 24

The materials used in Example 22 were reacted by the same conditions and procedure as Example 22 except that 5% vinyltrichlorosilane was mixed instead of 5% phenyltrichlorosilane. The yield of polysilamethylenosilane soluble in organic solvents was 93.0%, with mean molecular weight of 2,200. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm, and Si—CH=CH$_2$ at 6.0 ppm.

EXAMPLE 25

The materials used in Example 22 were reacted by the same conditions and procedure as Example 22 except that 5% allyltrichlorosilane was mixed instead of 5% phenyltrichlorosilane. The yield of polysilamethylenosilane soluble in organic solvents was 92.0%, with mean molecular weight of 1,900. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm, and Si—CH$_2$—CH=CH$_2$ at 5.0 and 5.8 ppm.

EXAMPLE 26

The materials used in Example 22 were reacted by the same conditions and procedure as Example 22 except that 5% trimethylsilylmethyltrichlorosilane was mixed instead of 5% phenyltrichlorosilane. The yield of polysilamethylenosilane soluble in organic solvents was 93.7%, with mean molecular weight of 2,300. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm.

EXAMPLE 27

The materials used in Example 1 were reacted by the same conditions and procedure as Example 1 except that the 50:50 mixture of 2,4,4,6-tetrachloro-2,6-dimethyl-2,4,6-trisilaheptane and 4,4-dichloro-2,2,6,6-tetramethyl-2,4,6-trisilaheptane in mole ratio was reacted. The yield of polysilamethylenosilane soluble in organic solvents was 92.7%, with mean molecular weight of 2,000. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$ and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 28

The materials used in Example 1 were reacted by the same conditions and procedure as Example 1 except that the 20:10:70 mixture of 2,4,4,6-tetrachloro-2,6-dimethyl-2,4,6-trisilaheptane, 4,4-dichloro-2,2,6,6-tetramethyl-2,4,6-trisilaheptane and dimethyldichlorosilane in mole ratio was reacted. The yield of polysilamethylenosilane soluble in organic solvents was 92.0%, with mean molecular weight of 2,700. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 29

The materials used in Example 28 were reacted by the same conditions and procedure as Example 28 except that the mixture of 2,4,4,6-tetrachloro-2,6-dimethyl-2,4,6-trisilaheptane, 4,4-dichloro-2,2,6,6-tetramethyl-2,4,6-trisilaheptane and dimethyldichlorosilane was 20:10:65 insted of 20:10:70 and 5% methyltrichlorosilane was additionally mixted therewith. The yield of polysilamethylenosilane was 87.6%, with mean molecular weight of 3,100. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were observed peaks corresponding to Si—CH$_3$ at 0.2 ppm, Si—CH$_2$—Si at 1.1 ppm, and Si—H at 4.0 ppm.

EXAMPLE 30

The materials used in Example 29 were reacted by the same conditions and procedure as Example 29 except that 5% vinylchlorosilane was mixed instead of 5% methyltrichlorosilane. The yield of polysilamethylenosilane soluble in organic solvents was 85.0%, mean with molecular weight of 4,100. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm, and Si—CH=CH$_2$ at 6.0 ppm.

EXAMPLE 31

The materials used in Example 29 were reacted by the same conditions and procedure as Example 29 except that 5% allhyltrichlorosilane was mixed instead of 5% methyltrichlorosilane. The yield of polysilamethylenosilane soluble in organic solvents was 90.0%, with mean molecular weight of 3,900. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm, and Si—CH$_2$—CH=CH$_2$ at 5.0 and 5.8 ppm.

EXAMPLE 32

The materials used in Example 29 were reacted by the same conditions and procedure as Example 29 except that 5% octadecyltrichlorosilane was mixed instead of 5% methyltrichlorosilane. The yield of polysilamethylenosilane soluble in organic solvents was 89.0%, with mean molecular weight of 2,800. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, and Si—H at 4.0 ppm.

EXAMPLE 33

The materials used in Example 29 were reacted by the same conditions and procedure as Example 29 except that 5% phenyltrichlorosilane was mixed instead of 5% methyltrichlorosilane. The yield of polysilamethylenosilane soluble in organic solvents was 83.0%, with mean molecular weight of 3,200. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm, and Si—Ph at 7.3 ppm.

EXAMPLE 34

The materials used in Example 23 were reacted by the same conditions and procedure as Example 23 except that tetrahydrofuran was added in amount of 20% by weight, on the basis of used toluene, instead of using only toluene as solvent. The yield of polysilamethylenosilane soluble in organic solvents was 82.0%, with mean molecular weight of 3,400. As the results of this product analysed by IR spectrometer were observed peaks corresponding to Si—H at 2090 cm$^{-1}$, Si—CH$_3$ at 1250 cm$^{-1}$, and Si—CH$_2$—Si at about 1000 and 1400 cm$^{-1}$, and by nuclear magnetic resonance spectrometry (60 MHz) were also observed peaks corresponding to Si—CH$_3$ at 0.2 ppm, Si—CH$_2$—Si at 1.1 ppm, Si—H at 4.0 ppm, and Si—C$_6$H$_{13}$ at 1.3 ppm.

What is claimed is:

1. A process for the preparation of polysilamethylenosilane polymers having formula III which comprises dechlorinating 2,4,6-trisilaheptanes having formula I, dimethyldichlorosilane and trichlorosilanes having formula II with sodium in the presence of toluene or mixture of toluene and tetrahydrofuran as solvent at the temperature in the range of 100° to 150° C.:

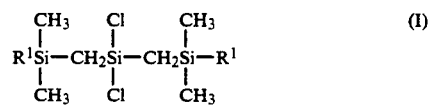

wherein, R$^1$ represents methyl or chlorine atom,

wherein, R$^2$ represents methyl, vinyl, allyl, octadecyl, cyclohexyl or trimethylsilylmethyl group,

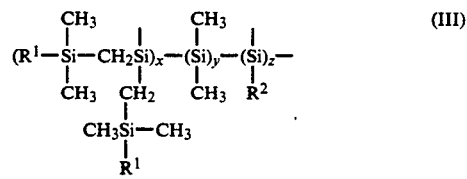

wherein, R$^1$ represents methyl or, when R$^1$ in formula I is chlorine, Si—Si bond, and R$^2$ is defined same as R$^2$ in formula II.

2. A process for the preparation of polysilamethylenosilane polymers having formula III which comprises dechlorinating 2,4,6-trisilaheptanes having formula I with sodium in the presence of toluene or mixture of toluene and tetrahydrofuran as solvent at the temperature in the range of 100° to 150° C.:

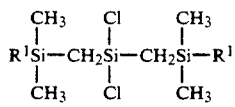

wherein, $R^1$ represents methyl or chlorine atom,

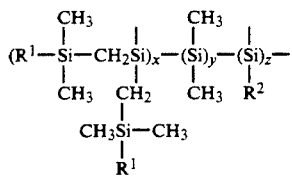

wherein, $R^1$ represents methyl or chlorine atom.

3. A process for the preparation of polysilamethylenosilane polymers having formula III which compries dechlorinating 2,4,6-trisilaheptanes having formula I and dimethyldichlorosilane with sodium in the presence of toluene or mixture of toluene and tetrahydrofuran as solvent at the temperature in the range of 100° to 150° C.:

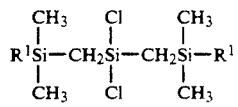

wherein, $R^1$ represents methyl or chlorine atom,

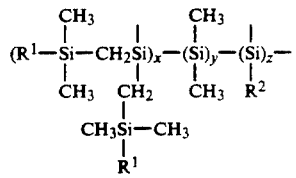

wherein, $R^1$ represents methyl or chlorine atom.

4. A process according to claim 1, characterized in that the addition ratio of 2,4,6-trisilaheptanes having formula I, dimethyldichlorosilane and trichlorosilanes having formula II consists of 20–50:40–75:5–15 in mole %.

5. A process according to claim 2, characterized in that in case of monomers of 2,4,6-trisilaheptanes having formula I, in which all $R^1$ represent methyl, and chlorine respectively, the addition ratio of both monomers consists of 50:50 in mole %.

6. A process according to claim 3, characterized in that the addition ratio of 2,4,6-trisilaheptanes having formula I and dimethyldichlorosilane consists of 8–80:20–92 in mole %.

* * * * *